United States Patent
Friesen et al.

(10) Patent No.: US 12,121,043 B2
(45) Date of Patent: *Oct. 22, 2024

(54) FEED ADDITIVE COMPOSITIONS

(71) Applicant: ELANCO US INC., Greenfield, IN (US)

(72) Inventors: Kim Friesen, Carthage, IN (US); Ran Song, Eden Prairie, MN (US); Robert Musser, Good Thunder, MN (US)

(73) Assignee: ELANCO US INC., Greenfield, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/123,632

(22) Filed: Mar. 20, 2023

(65) Prior Publication Data

US 2023/0371551 A1 Nov. 23, 2023

Related U.S. Application Data

(63) Continuation of application No. 16/139,621, filed on Sep. 24, 2018, now Pat. No. 11,638,434.

(60) Provisional application No. 62/595,160, filed on Dec. 6, 2017.

(51) Int. Cl.
*A23K 20/158* (2016.01)
*A23K 10/30* (2016.01)
*A23K 20/189* (2016.01)
*A23K 50/00* (2016.01)
*A23K 50/10* (2016.01)
*A23K 50/20* (2016.01)
*A23K 50/30* (2016.01)
*A23K 50/80* (2016.01)
*A61K 31/00* (2006.01)

(52) U.S. Cl.
CPC ............ *A23K 20/158* (2016.05); *A23K 10/30* (2016.05); *A23K 20/189* (2016.05); *A23K 50/00* (2016.05); *A23K 50/10* (2016.05); *A23K 50/20* (2016.05); *A23K 50/30* (2016.05); *A23K 50/80* (2016.05); *A61K 31/00* (2013.01)

(58) Field of Classification Search
CPC ...... A23K 20/189; A23K 50/80; A23K 50/20; A23K 50/10; A23K 10/30; A23K 20/158; A23K 50/00; A23K 50/30; A61K 31/00
USPC .......................................................... 426/630
See application file for complete search history.

(56) References Cited

U.S. PATENT DOCUMENTS

| | | |
|---|---|---|
| 4,851,226 A | 7/1989 | Julian et al. |
| 5,075,114 A | 12/1991 | Roche |
| 5,554,646 A | 9/1996 | Cook et al. |
| 5,876,759 A | 3/1999 | Gowan, Jr. |
| 2011/0130464 A1 | 6/2011 | Monahan et al. |
| 2014/0121275 A1 | 5/2014 | Hagen et al. |
| 2015/0007419 A1 | 1/2015 | Liu et al. |
| 2019/0166877 A1 | 6/2019 | Friesen et al. |

OTHER PUBLICATIONS

International Search Report and Written Opinion from International Application No. PCT/US18/054850, dated Dec. 4, 2018, 8 pages.
International Search Report and Written Opinion from International Application No. PCT/US18/054847, dated Jan. 15, 2019, 10 pages.
Irie M, "Effect of dietary supplementation of copper and kapok mail on fat characteristics of pigs" Asian-Australasian Journal of Animal Sciences, vol. 3, No. 1, pp. 33-38, Mar. 1, 1990.
Villela C., "Effects of adding minimally refined cottonseed oil or crude glycerol to diets containing 40% distillers dried grains with solubles (DOGS) on growth performance, carcass characteristics and pork fat quality of growing-finishing bigs, A thesis" The University of Minnesota; May 2016.
Maeda, K et al., "Effect of dietary kapok oil supplementation on growth performance, carcass trails, meat quality and sensory traits of pork in finishing-pigs." Animal Science Journal, vol. 88, No. 8 pp. 1066-1074, Aug. 2017.
Griswold, KE "Effectiveness of short-term feeding strategies for alternating conjugated linoleic acid content of beef" Journal of animal Science, vol. 81, No. 7, pp. 1862-1871, Aug. 1, 2003.
Wood, et al.; Backfat Quality in Boars and Barrows at 90 KG Live Weight; British Society of Animal Production; 1985; 40: 481-487; Great Britain.
Correa, et al.; Effects of Slaughter Weight on Carcass Composition and Meat Quality in Pigs of Two Different Growth Rates; Meat Science; 2006; 72: 91-99; Canada.
Wood, et al.; The Chemical Composition of Fat Tissues in the Pig: Effects of Castration and Feeding Treatment; Livestock Production Science; 1986; 15: 73-82.
Wood, et al.; Backfat Composition in Pigs: Differences Between Fat Thickness Groups and Sexes; Lifestock Production Science; 1989; 22: 351-362; Great Britain.
Lo Fiego, et al.; Influence of Genetic Type, Live Weight at Slaughter and Carcass Fatness on Fatty Acid Composition of Subcutaneous Adipose Tissue of Raw Ham in the Heavy Pig; Meat Science; 2005; 69: 107-114; Italy.

(Continued)

*Primary Examiner* — Subbalakshmi Prakash
(74) *Attorney, Agent, or Firm* — Barnes & Thornburg LLP

(57) ABSTRACT

The present disclosure provides feed composition comprising at least one cyclopropenoid fatty acids or at least one conjugated linoleic acid and at least one cyclopropenoid fatty acids with normal or basal feed. After administration of one of the feed compositions, improved health aspects, reduced health issues, reduced mortality, increased carcass gain and repartitioning nutrients to muscles, and controlled carcass iodine value in non-human animals as compared to a control group not fed with the feed composition.

14 Claims, No Drawings

(56) References Cited

OTHER PUBLICATIONS

Overholt, et al.; Comparison of Variability in Pork Carcass Composition and Quality Between Barros and Gilts; J. Anim. Sci.; 2016; 94: 4415-4426; United States.
Kellner, et al.; The Impact of Dietary Fat Withdrawal on Carcass Iodine Value, Belly Characteristics, and Changes in Body Fat Over Time; J. Anim. Sci.; 2015; 93: 247-257; United States.
Batorek, et al.; Meta-Analysis of the Effect of Immunocastration on Production Performance, Reproductive Organs and Boar Taint Compounds in Pigs; The Animal Consortium; 2012; 6:8, pp. 1330-1338; France.
Eggert, et al.; Effects of Supplementing With Soybean Oil and Finishing With Beef Tallow on Pork Quality and Carcass Composition; Purdue University 1998 Swine Day Report; 1998; United States.
Goehring; Investigation of Factors That Influence Belly Quality and of Cooked Bacon Characteristics; Department of Animal Sciences and Industry College of Agriculture, Kansas State University, Manhattan, Kansas; 2015; United States.
Dunshea, et al.; A Review—Fat Deposition and Metabolism in the Pig; Department of of Primary Industries, Department of Agriculture; 2003; Australia.
Kennedy, et al.; Antiobesity Mechanisms of Action of Conjugated Linoleic Acid; J. Nutr. Biochem; Mar. 2010; 21(3): 171-179; United States.
Lehnen et al.; A Review on Effects of Conjugated Linoleic Fatty Acid (CLA) Upon Body Composition and Energetic Metabolism; Journal of the International Society of Sports Nutrition; 2015; 12:36.
Gomez, et al.; Effects of Sterculicacid on Stearoyl-CoA Communications; 2003; 300: 316-326; United States.
Widmer, et al.; Effects of Feeding Distillers Dried Grains With Solubles, High-Protein Distillers Dried Grains, and Corn Germ to Growing-Finishing Pigs on Pig Performance, Carcas Quality, and the Palatability of Port; J. Anim. Sci.; 2008; 86: 1819-1831; United States.
Xu, et al.; Effects of Feeding Diets Containing Increasing Content of Corn Distillers Dried Grains With Solubles to Grower-Finisher Pigs on Growth Performance, Carcass Composition, and Port Fat Quality; J. Anim. Sci.; 2010; 88: 1398-1410; United States.
Davis, et al.; Effects of Adding Supplemental Tallow to Diets Containing 30% Distillers Dried Grains With Solubles on Growth Performance, Carcass Characteristics, and Port Fat Quality in Growing-Finishing Pigs; American Society of Animal Sciences; 2015; 93: 266-277; United States.
Mu et al. Food Sci Nutr. 2019;7:2436-2447. (Year: 2019).

FEED ADDITIVE COMPOSITIONS

CROSS REFERENCE TO RELATED APPLICATIONS

The present application is a continuation application of U.S. patent application Ser. No. 16/139,621, filed Sep. 24, 2018, now U.S. Pat. No. 11,638,434, which claims benefit under 35 U.S.C. § 119 of U.S. Provisional Patent Application No. 62/595,160, entitled, "FEED ADDITIVE COMPOSITIONS COMPRISING CYCLOPROPENOIC FATTY ACIDS AND CONJUGATED LINOLEIC ACID AND METHODS TO ENHANCE GROWTH PERFORMANCE AND CARCASS QUALITY IN PIGS," filed Dec. 6, 2017, the entirety of both which is incorporated herein by reference.

FIELD OF THE INVENTION

The present disclosure generally relates to feed compositions and methods for improving health aspects, reducing health issues, reducing mortality, increasing carcass gain and repartitioning nutrients to muscles, and controlling the carcass iodine value in non-human animals.

BACKGROUND OF THE INVENTION

Animal husbandry is a branch of agriculture concerned with raising, breeding, and day to day care of animals. Famers engaged in this branch of agriculture produce meat, eggs, milk, and other products for the consumer. Additionally, these farmers are engaged in breeding and raising a wide variety of animals.

Aquaculture and mariculture is another branch of agriculture focused with raising, breeding, raising, and care of aquatic creatures. These farmers are concerned with producing products from these creatures including fish and oil derived from these creatures.

Famers engaged in animal husbandry, aquaculture, and mariculture face many challenges. The demand for food and food products from these branches of agriculture is anticipated to increase significantly as the population is growing. Also, with the increase in population, increased demands on land, water, and energy resources are being realized. Global environmental challenges, including global climate change, and the growing threat of disease transmission to and from agricultural animals adds further challenges. Therefore, farmers need to become more efficient, produce the products at a higher rate, and at an increased rate to meet market challenges. Additionally, farmers need a low cost method to produce these products since the profit margin is these areas can be quite low.

U.S. Pat. No. 9,538,774 describes feeding a diet supplemented with DDGS (Distiller's dried grains with solubles) or another supplement containing UFA at a level above a threshold to animals such as swine, cattle, and poultry can have negative effects on carcass fat, certain growth parameters, and meat characteristics. When a supplement is further provided with a second supplement containing cyclopropenoid fatty acid, the negative effects otherwise expected are wholly or at least partially countered. Additionally, U.S. Pat. No. 9,538,774 further discloses the negative effects on carcass characteristics caused by ractopamine. This negative effect can also be countered by the addition of this amount of at least one source of CPFA in the diet.

To meet these challenges, what is needed is a feed composition which is generally low cost but also enhances health, enhances growth aspects, and improves the health of animals and aquatic creatures.

SUMMARY OF THE INVENTION

Provided herein are feed compositions useful for non-human animals, methods for improving health aspects, reducing health issues, reducing mortality, increasing carcass gain and repartitioning nutrients to muscles, and controlling the carcass iodine value by a feed composition wherein the feed composition is orally administered to the non-human animal at least once per day.

In one aspect, a feed composition comprising the at least one conjugated linoleic acid (CLA) and the at least one cyclopropenoid fatty acid (CPFA) is provided.

In another aspect, methods for improving health aspects in a non-human animal by administering a feed composition comprising the at least one conjugated linoleic acid (CLA) and the at least one cyclopropenoid fatty acid (CPFA) are provided.

In an additional aspect, methods for increasing carcass gain and repartitioning nutrients to muscles in a non-human animal by administering a feed composition comprising the at least one conjugated linoleic acid (CLA) and the at least one cyclopropenoid fatty acid (CPFA) are provided.

In yet another aspect, methods for controlling the iodine value (IV) in a non-human animal by administering a feed composition comprising the at least one conjugated linoleic acid (CLA) and the at least one cyclopropenoid fatty acid (CPFA) are provided.

In still another aspect, methods for increasing carcass gain and repartitioning nutrients to muscles in a non-human animal by administering a feed composition comprising the at least one cyclopropenoid fatty acid (CPFA) are provided.

Other features and iterations of the invention are described in more detail below.

DETAILED DESCRIPTION OF THE INVENTION

The present invention relates to feed compositions useful for non-human animals. The feed compositions comprise the at least one conjugated linoleic acid and the at least one cyclopropenoid fatty acids. Administration of the feed composition to non-human animals at least once per day exhibits a synergistic effect by improving health aspects, reducing health issues, reduced mortality, increasing carcass gain and repartitioning nutrients to muscles, and controlling the carcass iodine value as compared to a control group not administered the feed composition or administered a feed composition containing only conjugated linoleic acid or only cyclopropenoid fatty acids.

(I) Feed Compositions

One aspect of the present disclosure encompasses feed compositions for oral administration to non-human animals. The feed composition comprises at least one conjugated linoleic acid (CLA) and at least one cyclopropenoid fatty acid (CPFA). Basal feeds may be also added to the feed composition. Other optional additives may be further included in the feed composition. The at least one conjugated linoleic acid (CLA) and at least one cyclopropenoid fatty acid (CPFA) may be formulated with animal feed, or added to normal animal feed before administration to the non-human animals at least once per day. The feed composition comprising a combination of at least one CLA and at least one CPFA provides a synergistic effect by improving health aspects, reducing health issues, reduced mortality, increasing carcass gain and repartitioning nutrients to muscles, and controlling the carcass iodine value as compared to a control group not administered the feed composition.

(a) At Least One Conjugated Linoleic Acid

In some embodiments, the feed composition comprises at least one conjugated linoleic acid. In other embodiments, the feed composition does not contain conjugated linoleic acid. Non-limiting examples of useful conjugated linoleic acids may be cis-9, trans-11-octadecadienoic acid, trans-10, cis-12-octadecadienoic acid, or combinations thereof. As appreciated by the skilled artisan, the at least one conjugated linoleic acid described herein may be obtained from a number of different sources. In various embodiments, the at least one conjugated linoleic acid may be synthetically derived, extracted or prepared from a natural substance, obtained from bacterial fermentation, derived from algae, or combinations thereof. Generally, the form of the at least one conjugated linoleic acid may be a pure liquid, a suitable acceptable salt of the at least one conjugated linoleic acid, an oil comprising the at least one conjugated linoleic acid, or combinations thereof.

Generally, the natural source of the at least one conjugated linoleic acid may be a plant source, an animal source, an algae source, a seafood source, or combinations thereof. For a plant source, the conjugated linoleic acid may be, but are not limited to, a flower, an unprocessed seed, a processed seed, an oil derived from the plant, flower, or seed, or a meal derived from the plant, flower, or the seed. Non-limiting examples of plant sources may be mushrooms, safflower, sunflowers, coconuts, sesame, pomegranate, olives, soy, corn, canola, hemp, flax, and various nuts such as pine nuts, pecans; and Brazil nuts, or combinations thereof. For an animal source, the conjugated linoleic acid may be, but are not limited to, derived from dairy products and meat from ruminant animals. Non-limiting examples of the sources may be milk, butter, yogurt, cheese, ground beef, veal, lamb, pork, chicken, turkey, cottage cheese, or combinations thereof. For an algae source, the at least one conjugated linoleic acid may be any algae that comprises conjugated linoleic acid. For a seafood source, the at least one conjugated linoleic acid may be a fish, fish meal, fish oil, or combinations thereof. Non-limiting examples of suitable fish may be, but are not limited to, abalone scallops, albacore tuna, anchovies, catfish, clams, cod, gem fish, herring, lake trout, mackerel, menhaden, orange roughy, salmon, sardines, sea mullet, sea perch, shark, shrimp, squid, trout, tuna, and combinations thereof.

Non-limiting sources of the at least one conjugated linoleic acid may be mushrooms, dairy products and meat from ruminants; sources from fish such as salmon; derived from flowers, seeds, oils, and meals obtained from safflower, sunflowers, coconuts, sesame, pomegranate, olives, soy, corn, canola, hemp, flax, and derived from nuts, oils, and meals from various nuts such as pine nuts, pecans; and Brazil nuts, or combinations thereof.

In some embodiments, the oil comprising the at least one conjugated linoleic acid may be used in the feed composition. In general, the oil comprising the at least one conjugated linoleic acid may range from about 20 weight % to about 80 weight % conjugated linoleic acid. In various embodiments, the oil comprising the at least one conjugated linoleic acid may range from about 20 weight % to about 80 weight %, from about 30 weight % to about 70 weight %, from about 40 weight % to about 60 weight %, or from about 45 weight % to about 55 weight %. As appreciated by the skilled artisan, the weight % of the oil comprising the at least one conjugated linoleic acid depends on the natural source of the at least one conjugated linoleic acid and the method for preparing the oil.

An effective amount of the at least one conjugated linoleic acid in a feed composition can and will vary depending on the body weight, sex, and/or medical condition of the non-human animal, as well as the species of the non-human animal, and may be determined experimentally using methods known in the art. Generally, the amount of the at least one conjugated linoleic acid in the feed composition may range from about 0.56 lb/ton to 5.6 lb/ton. In various embodiments, the amount of the at least one conjugated linoleic acid in the feed composition may range from about 0.56 lb/ton to 5.6 lb/ton, from about 1.12 lb/ton to 5.0 lb/ton, or from about 2.24 lb/ton to about 4.48 lb/ton. In an embodiment, the effective amount of the at least one conjugated linoleic acid in a feed composition may range from about 2.24 lb/ton to about 4.48 lb/ton.

(b) At Least One Cyclopropenoid Fatty Acid

In some embodiments, the feed composition further comprises at least one cyclopropenoid fatty acid. In other embodiments, the feed composition consists of cyclopropenoid fatty acid and optional additives, described below. Non-limiting examples of cyclopropenoid fatty acids may be sterulic acid, malvalic acid, dihydrosterculic acid, or combinations thereof. As appreciated by the skilled artisan, the at least one cyclopropenoid fatty acid may be obtained from a number of different sources. Generally, the natural source of cyclopropenoid fatty acid may be a plant source contained in the flower, an unprocessed seed, a processed seed, an oil derived from the plant, algae, flower, or seed, or a meal derived from the plant, algae, flower, or the seed. Non-limiting examples of plant sources may be, but not limited to, oilseed crops, such as, rape (canola), sunflower, safflower, soybean, cotton, cotton palm, corn, olive, sesame, corn, peanuts, flax, kapok, or combinations thereof. Generally, the at least one cyclopropenoid fatty acid may be present in the composition a pure liquid, a suitable acceptable salt of the at least one conjugated linoleic acid, an oil comprising the at least one conjugated linoleic acid, or combinations thereof.

In some embodiments, oil comprising the at least one cyclopropenoid fatty acid may be used in the feed composition. In general, the oil comprising the at least one cyclopropenoid fatty acid may range from about 10 weight % to about 60 weight % cyclopropenoid fatty acid. In various embodiments, the oil comprising the at least one cyclopropenoid fatty acid may range from about 10 weight % to about 60 weight %, from about 20 weight % to about 50 weight %, from about 30 weight % to about 45 weight %, or from about 38 weight % to about 42 weight %. In a preferred embodiment, oil comprising the at least one cyclopropenoid fatty acid may range from about 13 weight % to about 50 weight %. As appreciated by the skilled artisan, the weight % of the oil comprising the at least one cyclopropenoid fatty acid depends on the natural source of the cyclopropenoid fatty acid and the method for preparing the oil.

An effective amount of the at least one cyclopropenoid fatty acid present in a feed composition can and will vary depending on the body weight, sex, and/or medical condition of the non-human animal, as well as the species of the non-human animal, and may be determined experimentally using methods known in the art. Generally, the effective amount of the at least one cyclopropenoid fatty acids in the feed composition may range from about 30 gram/ton to about 306 gram/ton. In various embodiments, the effective amount of the at least one cyclopropenoid fatty acid in the feed composition may range from about 30 gram/ton to about 306 gram/ton, from about 50.0 g/ton to 275 g/ton, or from about 90 g/ton to about 245 g/ton. In an embodiment, an effective amount of the at least one cyclopropenoid fatty acid in a feed composition may range from about 90 gram/ton to 245 gram/ton.

(c) Normal Animal Feed/Basal Feed

"Normal feed" or "feed matter" as defined herein refers to a normal general feed provided to the non-human animals. "Basal feed" as defined herein refers to animal feeds which comprise concentrated sources of energy and are especially rich in starches and sugars. Basal feeds may include the whole group of grains (e.g. wheat, maize, oats, etc.) and their by-products. Generally, basal feeds have a protein content that is greater than 16% and a maximum fiber content of 18%. The main difference between basal feeds and other feed stuffs is that basal feeds have high digestible energy content.

The basal feed may be included in the feed composition. Additionally, normal or basal feeds may include one or more additional components. Non-limiting examples these components may include, without limitation: corn or a component of corn, such as, for example, corn meal, corn fiber, corn hulls, corn DDGS (distiller's dried grain with solubles), silage, ground coin, corn germ, corn gluten, corn oil, or any other portion of a corn plant; soy or a component of soy, such as, for example, soy oil, soy meal, soy hulls, soy silage, ground soy, or any other portion of a soy plant; wheat or any component of wheat, such as, for example, wheat meal, wheat fiber, wheat hulls, wheat chaff, ground wheat, wheat germ, or any other portion of a wheat plant; canola or any other portion of a canola plant, such as, for example, canola oil, canola meal, canola protein, canola hulls, ground canola, or any other portion of a canola plant; sunflower or a component of a sunflower plant; sorghum or a component of a sorghum plant; sugar beet or a component of a sugar beet plant; cane sugar or a component of a sugarcane plant; barley or a component of a barley plant; palm oil, palm kernel or a component of a palm plant; glycerol; corn steep liquor; a waste stream from an agricultural processing facility; lecithin; rumen protected fats; molasses; soy molasses; flax; peanuts; peas; oats; grasses, such as orchard grass and fescue; fish meal, meat & bone meal; feather meal; and poultry byproduct meal; and alfalfa and/or clover used for silage or hay, and various combinations of any of the feed ingredients set forth herein, or other feed ingredients generally known in the art.

(d) Optional Additives

As will be recognized in the art, a feed composition may further be supplemented with amino acids, vitamins, minerals, and other feed additives such as other types of enzymes, organic acids, essential oils, probiotics, prebiotics, antioxidants, pigments, anti-caking agents, and the like which are detailed below.

(i) Vitamins

Optionally, the normal animal feed or basal feed may include one or more vitamins. Suitable vitamins for use in the dietary supplement include vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

The normal animal feed or basal feed may include one or more forms of an effective amount of any of the vitamins described herein or otherwise known in the art. Exemplary vitamins include vitamin K, vitamin D, vitamin C, and biotin. An "effective amount" of a vitamin typically quantifies an amount at least about 10% of the United States Recommended Daily Allowance ("RDA") of that particular vitamin for a subject. It is contemplated, however, that amounts of certain vitamins exceeding the RDA may be beneficial for certain animals. For example, the amount of a given vitamin may exceed the applicable RDA by 100%, 200%, 300%, 400%, 500% or more.

(ii) Minerals

Generally, the normal animal feed or basal feed may include one or more minerals or mineral sources. Non-limiting examples of minerals include, without limitation, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

Generally speaking, the normal animal feed or basal feed may include one or more forms of an effective amount of any of the minerals described herein or otherwise known in the art. An "effective amount" of a mineral typically quantifies an amount at least about 10% of the United States Recommended Daily Allowance ("RDA") of that particular mineral for a subject. It is contemplated, however, that amounts of certain minerals exceeding the RDA may be beneficial for certain subjects. For example, the amount of a given mineral may exceed the applicable RDA by 100%, 200%, 300%, 400%, 500% or more. Typically, the amount of mineral included in the dietary supplement may range from about 1 mg to about 1500 mg, about 5 mg to about 500 mg, or from about 50 mg to about 500 mg per dosage.

(iii) Essential Fatty Acids

Optionally, the normal animal feed or basal feed may include a source of an essential fatty acid. The essential fatty acid may be isolated or it may be an oil source or fat source that contains an essential fatty acid. In one embodiment, the essential fatty acid may be a polyunsaturated fatty acid (PUFA), which has at least two carbon-carbon double bonds generally in the cis-configuration. The PUFA may be a long chain fatty acid having at least 18 carbons atoms. The PUFA may be an omega-3 fatty acid in which the first double bond occurs in the third carbon-carbon bond from the methyl end of the carbon chain (i.e., opposite the carboxyl acid group). Examples of omega-3 fatty acids include alpha-linolenic acid (18:3, ALA), stearidonic acid (18:4), eicosatetraenoic acid (20:4), eicosapentaenoic acid (20:5; EPA), docosatetraenoic acid (22:4), n-3 docosapentaenoic acid (22:5; n-3DPA), and docosahexaenoic acid (22:6; DHA). The PUFA may also be an omega-5 fatty acid, in which the first double bond occurs in the fifth carbon-carbon bond from the methyl end. Exemplary omega-5 fatty acids include myristoleic acid (14:1), myristoleic acid esters, and cetyl myristoleate. The PUFA may also be an omega-6 fatty acid, in which the first double bond occurs in the sixth carbon-carbon bond from the methyl end. Examples of omega-6 fatty acids include linoleic acid (18:2), gamma-linolenic acid (18:3), eicosadienoic acid (20:2), dihomo-gamma-linolenic acid (20:3), arachidonic acid (20:4), docosadienoic acid (22:2), adrenic acid (22:4), and n-6 docosapentaenoic acid (22:5). The fatty acid may also be an omega-9 fatty acid, such as oleic acid (18:1), eicosenoic acid (20:1), mead acid (20:3), erucic acid (22:1), and nervonic acid (24:1).

In another embodiment, the essential fatty acid source may be a seafood-derived oil. The seafood may be a vertebrate fish or a marine organism, such that the oil may be fish oil or marine oil. The long chain (20C, 22C) omega-3 and omega-6 fatty acids are found in seafood. The ratio of omega-3 to omega-6 fatty acids in seafood ranges from about 8:1 to 20:1. Seafood from which oil rich in omega-3 fatty acids may be derived include, but are not limited to, abalone scallops, albacore tuna, anchovies, catfish, clams, cod, gem fish, herring, lake trout, mackerel, menhaden, orange roughy, salmon, sardines, sea mullet, sea perch, shark, shrimp, squid, trout, and tuna.

In yet another embodiment, the essential fatty acid source may be a plant-derived oil. Plant and vegetable oils are rich in omega-6 fatty acids. Some plant-derived oils, such as flaxseed oil, are especially rich in omega-3 fatty acids. Plant or vegetable oils are generally extracted from the seeds of a plant, but may also be extracted from other parts of the plant. Plant or vegetable oils that are commonly used for cooking or flavoring include, but are not limited to, acai oil, almond oil, amaranth oil, apricot seed oil, argan oil, avocado seed oil, babassu oil, ben oil, blackcurrant seed oil, Borneo tallow nut oil, borage seed oil, buffalo gourd oil, canola oil, carob pod oil, cashew oil, castor oil, coconut oil, coriander seed oil, corn oil, cottonseed oil, evening primrose oil, false flax oil, flax seed oil, grapeseed oil, hazelnut oil, hemp seed oil, kapok seed oil, lallemantia oil, linseed oil, macadamia oil, meadowfoam seed oil, mustard seed oil, okra seed oil, olive oil, palm oil, palm kernel oil, peanut oil, pecan oil, pequi oil, perilla seed oil, pine nut oil, pistachio oil, poppy seed oil, prune kernel oil, pumpkin seed oil, quinoa oil, ramtil oil, rice bran oil, safflower oil, sesame oil, soybean oil, sunflower oil, tea oil, thistle oil, walnut oil, or wheat germ oil. The plant derived oil may also be hydrogenated or partially hydrogenated.

In still a further embodiment, the essential fatty acid source may be an algae-derived oil. Commercially available algae-derived oils include those from *Crypthecodinium cohnii* and *Schizochytrium* sp. Other suitable species of algae, from which oil is extracted, include *Aphanizomenon flos-aquae, Bacilliarophy* sp., *Botryococcus braunii, Chlorophyceae* sp., *Dunaliella tertiolecta, Euglena gracilis, Isochrysis galbana, Nannochloropsis salina, Nannochloris* sp., *Neochloris oleoabundans, Phaeodactylum tricornutum, Pleurochrysis carterae, Prymnesium parvum, Scenedesmus dimorphus, Spirulina* sp., and *Tetraselmis chui*.

(iv) Amino Acids

The normal animal feed or basal feed may optionally include from one to several amino acids. Suitable amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs. In certain embodiments, the amino acid will be selected from the essential amino acids. An essential amino acid is generally described as one that cannot be synthesized de novo by the organism, and therefore, must be provided in the diet. By way of non-limiting example, the essential amino acids for humans include: L-histidine, L-isoleucine, L-leucine, L-lysine, L-methionine, L-phenylalanine, L-valine and L-threonine.

(v) Antioxidants

The normal animal feed or basal feed may include one or more suitable antioxidants. As will be appreciated by a skilled artisan, the suitability of a given antioxidant will vary depending upon the species to which the dietary supplement will be administered. Non-limiting examples of antioxidants include ascorbic acid and its salts, ascorbyl palmitate, ascorbyl stearate, anoxomer, N-acetylcysteine, benzyl isothiocyanate, o-, m- or p-amino benzoic acid (o is anthranilic acid, p is PABA), butylated hydroxyanisole (BHA), butylated hydroxytoluene (BHT), caffeic acid, canthaxantin, alpha-carotene, beta-carotene, beta-carotene, beta-apo-carotenoic acid, carnosol, carvacrol, catechins, cetyl gallate, chlorogenic acid, citric acid and its salts, p-coumaric acid, curcurin, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eugenol, ferulic acid, flavonoids, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytyrosol, hydroxyurea, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, propyl gallate, polyphosphates, quercetin, trans-resveratrol, rosmarinic acid, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, zeaxanthin, or combinations thereof.

Natural antioxidants that may be included in the dietary supplement include, but are not limited to, apple peel extract, blueberry extract, carrot juice powder, clove extract, coffee berry, coffee bean extract, cranberry extract, eucalyptus extract, ginger powder, grape seed extract, green tea, olive leaf, parsley extract, peppermint, pimento extract, pomace, pomegranate extract, rice bran extract, rosehips, rosemary extract, sage extract, tart cherry extract, tomato extract, tumeric, and wheat germ oil.

(vi) Anti-Inflammatory Agents

The normal animal feed or basal feed may optionally include at least one anti-inflammatory agent. In one embodiment, the anti-inflammatory agent may be a synthetic non-steroidal anti-inflammatory drug (NSAID) such as acetylsalicylic acid, dichlophenac, indomethacin, oxamethacin, ibuprofen, indoprofen, naproxen, ketoprofen, mefamanic acid, metamizole, piroxicam, and celecoxib. In an alternate embodiment, the anti-inflammatory agent may be a prohormone that modulates inflammatory processes. Suitable prohormones having this property include prohormone convertase 1, proopiomelanocortin, prohormone B-type natriuretic peptide, SMR1 prohormone, and the like. In another embodiment, the anti-inflammatory agent may be an enzyme having anti-inflammatory effects. Examples of anti-inflammatory enzymes include bromelain, papain, serrapeptidase, and proteolytic enzymes such as pancreatin (a mixture of tyrpsin, amylase and lipase).

In still another embodiment, the anti-inflammatory agent may be a peptide with anti-inflammatory effects. For example, the peptide may be an inhibitor of phospholipase A2, such as antiflammin-1, a peptide that corresponds to amino acid residues 246-254 of lipocortin; antiflammin-2, a peptide that corresponds to amino acid residues 39-47 of uteroglobin; S7 peptide, which inhibits the interaction between interleukin 6 and interleukin 6 receptor; RP1, a prenyl protein inhibitor; and similar peptides. Alternatively, the anti-inflammatory peptide may be cortistatin, a cyclic neuropeptide related to somatostatin, or peptides that correspond to an N-terminal fragment of SV-IV protein, a conserved region of E-, L-, and P-selectins, and the like. Other suitable anti-inflammatory preparations include collagen hydrolysates and milk micronutrient concentrates (e.g., MicroLactin® available from Stolle Milk Biologics, Inc., Cincinnati, OH), as well as milk protein hydrolysates, casein hydrolysates, whey protein hydrolysates, and plant protein hydrolysates.

In a further embodiment, the anti-inflammatory agent may be a probiotic that has been shown to modulate inflammation. Suitable immunomodulatory probiotics include lactic acid bacteria such as acidophilli, lactobacilli, and bifidophilli. In yet another embodiment, the anti-inflammatory agent may be a plant extract having anti-inflammatory properties. Non-limiting examples of suitable plant extracts with anti-inflammatory benefits include blueberries, boswella, black catechu and Chinese skullcap, celery seed, chamomile, cherries, devils claw, eucalyptus, evening primrose, ginger, hawthorne berries, horsetail, Kalopanax pictus bark, licorice root, tumeric, white wallow, willow bark, and yucca.

(vii) Herbals

The normal animal feed or basal feed may optionally include at least one herb or herbal derivative. Suitable herbals and herbal derivatives, as used herein, refer to herbal extracts, and substances derived from plants and plant parts, such as leaves, flowers and roots, without limitation. Non-limiting exemplary herbals and herbal derivatives include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, capsicum, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. John's wort, sarsaparilla, sassafras, saw palmetto, skullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca and combinations thereof.

(viii) Pigments

The normal animal feed or basal feed may optionally include at least one pigment. Suitable non-limiting pigments include actinioerythrin, alizarin, alloxanthin, $\beta$-apo-2'-carotenal, apo-2-lycopenal, apo-6'-lycopenal, astacein, astaxanthin, azafrinaldehyde, aacterioruberin, aixin, $\alpha$-carotine, $\beta$-carotine, $\gamma$-carotine, $\beta$-carotenone, canthaxanthin, capsanthin, capsorubin, citranaxanthin, citroxanthin, crocetin, crocetinsemialdehyde, crocin, crustaxanthin, cryptocapsin, $\alpha$-cryptoxanthin, $\beta$-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-$\alpha$-carotenone, semi-$\beta$-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, $\alpha$-zeacarotene, or combinations thereof.

(ix) Pharmaceutical Acceptable Agents

The normal animal feed or basal feed may optionally include at least one pharmaceutical acceptable agent. Suitable non-limiting pharmaceutically acceptable agents include an acid/alkaline-labile drug, a pH dependent drug, or a drug that is a weak acid or a weak base. Examples of acid-labile drugs include statins (e.g., pravastatin, fluvastatin and atorvastatin), antibiotics (e.g., penicillin G, ampicillin, streptomycin, erythromycin, clarithromycin and azithromycin), nucleoside analogs (e.g., dideoxyinosine (ddI or didanosine), dideoxyadenosine (ddA), dideoxycytosine (ddC)), salicylates (e.g., aspirin), digoxin, bupropion, pancreatin, midazolam, and methadone. Drugs that are only soluble at acid pH include nifedipine, emonapride, nicardipine, amosulalol, noscapine, propafenone, quinine, dipyridamole, josamycin, dilevalol, labetalol, enisoprost, and metronidazole. Drugs that are weak acids include phenobarbital, phenytoin, zidovudine (AZT), salicylates (e.g., aspirin), propionic acid compounds (e.g., ibuprofen), indole derivatives (e.g., indomethacin), fenamate compounds (e.g., meclofenamic acid), pyrrolealkanoic acid compounds (e.g., tolmetin), cephalosporins (e.g., cephalothin, cephalaxin, cefazolin, cephradine, cephapirin, cefamandole, and cefoxitin), 6-fluoroquinolones, and prostaglandins. Drugs that are weak bases include adrenergic agents (e.g., ephedrine, desoxyephedrine, phenylephrine, epinephrine, salbutamol, and terbutaline), cholinergic agents (e.g., physostigmine and neostigmine), antispasmodic agents (e.g., atropine, methantheline, and papaverine), curariform agents (e.g., chlorisondamine), tranquilizers and muscle relaxants (e.g., fluphenazine, thioridazine, trifluoperazine, chlorpromazine, and triflupromazine), antidepressants (e.g., amitriptyline and nortriptyline), antihistamines (e.g., diphenhydramine, chlorpheniramine, dimenhydrinate, tripelennamine, perphenazine, chlorprophenazine, and chlorprophenpyridamine), cardioactive agents (e.g., verapamil, diltiazem, gallapomil, cinnarizine, propranolol, metoprolol and nadolol), antimalarials (e.g., chloroquine), analgesics (e.g., propoxyphene and meperidine), antifungal agents (e.g., ketoconazole and itraconazole), antimicrobial agents (e.g., cefpodoxime, proxetil, and enoxacin), caffeine, theophylline, and morphine. In another embodiment, the drug may be a biphosphonate or another drug used to treat osteoporosis. Non-limiting examples of a biphosphonate include alendronate, ibandronate, risedronate, zoledronate, pamidronate, neridronate, olpadronate, etidronate, clodronate, and tiludronate. Other suitable drugs include estrogen, selective estrogen receptor modulators (SERMs), and parathyroid hormone (PTH) drugs. In yet another embodiment, the drug may be an antibacterial agent. Suitable antibiotics include aminoglycosides (e.g., amikacin, gentamicin, kanamycin, neomycin, netilmicin, streptomycin, and tobramycin), carbecephems (e.g., loracarbef), a carbapenem (e.g., certapenem, imipenem, and meropenem), cephalosporins (e.g., cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone), macrolides (e.g., azithromycin, clarithromycin, dirithromycin, erythromycin, and troleandomycin), monobactam, penicillins (e.g., amoxicillin, ampicillin, carbenicillin, cloxacillin, dicloxacillin, nafcillin, oxacillin, penicillin G, penicillin V, piperacillin, and ticarcillin), polypeptides (e.g., bacitracin, colistin, and polymyxin B), quinolones (e.g., ciprofloxacin, enoxacin, gatifloxacin, levofloxacin, lomefloxacin, moxifloxacin, norfloxacin, ofloxacin, and trovafloxacin), sulfonamides (e.g., mafenide, sulfacetamide, sulfamethizole, sulfasalazine, sulfisoxazole, and trimethoprimsulfamethoxazole), and tetracyclines (e.g., demeclocycline, doxycycline, minocycline, and oxytetracycline). In an alternate embodiment, the drug may be an antiviral protease inhibitor (e.g., amprenavir, fosamprenavir, indinavir, lopinavir/ritonavir, ritonavir, saquinavir, and nelfinavir). In still another embodiment, the drug may be a cardiovascular drug. Examples of suitable cardiovascular agents include cardiotonic agents (e.g., digitalis (digoxin), ubidecarenone, and dopamine), vasodilating agents (e.g., nitroglycerin, captopril, dihydralazine, diltiazem, and isosorbide dinitrate), antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril), beta blockers (e.g., levobunolol, pindolol, timolol maleate, bisoprolol, carvedilol, and butoxamine), alpha blockers (e.g., doxazosin, prazosin, phenoxybenzamine, phentolamine, tamsulosin, alfuzosin, and terazosin), calcium channel blockers (e.g., amlodipine, felodipine, nicardipine, nifedipine, nimodipine, nisoldipine, nitrendipine, lacidipine, lercanidipine, verapamil, gallopamil, and diltiazem), and anticlot agents (e.g., dipyrimadole).

(x) Excipients

A variety of commonly used excipients in normal animal feed or basal feed may be selected on the basis of compatibility with the active ingredients. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, taste masking agents, an effervescent disintegration agent, and combinations of any of these agents.

In one embodiment, the excipient is a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof. The polypeptide may be any arrangement of amino acids ranging from about 100 to about 300,000 daltons.

In another embodiment, the excipient may be a filler. Suitable fillers include carbohydrates, inorganic compounds, and polyvinylpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may comprise a non-effervescent disintegrant. Suitable examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In another embodiment, the excipient may be an effervescent disintegrant. By way of non-limiting example, suitable effervescent disintegrants include sodium bicarbonate in combination with citric acid and sodium bicarbonate in combination with tartaric acid.

The excipient may comprise a preservative. Suitable examples of preservatives include antioxidants, such as α-tocopherol or ascorbate, and antimicrobials, such as parabens, chlorobutanol or phenol.

In another embodiment, the excipient may include a diluent. Diluents suitable for use include pharmaceutically acceptable saccharide such as sucrose, dextrose, lactose, microcrystalline cellulose, fructose, xylitol, and sorbitol; polyhydric alcohols; a starch; pre-manufactured direct compression diluents; and mixtures of any of the foregoing.

The excipient may include flavors. Flavors incorporated into the outer layer may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oil, such as lemon oil, orange oil, grape and grapefruit oil, fruit essences including apple, peach, pear, strawberry, raspberry, cherry, plum, pineapple, and apricot.

In another embodiment, the excipient may include a sweetener. By way of non-limiting example, the sweetener may be selected from glucose (coin syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia rebaudiana* (Stevioside); chloro derivatives of sucrose such as sucralose; sugar alcohols such as sorbitol, mannitol, sylitol, and the like.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

Depending upon the embodiment, it may be desirable to provide a coloring agent in the outer layer. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants, may be suitable for use in the present invention depending on the embodiment.

The excipient may include a taste-masking agent. Taste-masking materials include, e.g., cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcellulose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other embodiments, additional taste-masking materials contemplated are those described in U.S. Pat. Nos. 4,851,226, 5,075,114, and 5,876,759, each of which is hereby incorporated by reference in its entirety.

In various embodiments, the excipient may include a pH modifier. In certain embodiments, the pH modifier may include sodium carbonate or sodium bicarbonate.

Additionally, the antimicrobial clay may simply be added to any dosage form of a normal animal feed or basal feed.

The amount and types of ingredients (i.e., metal chelate, chondro protective agents, vitamin, mineral, amino acid, antioxidant, yeast culture, and essential fatty acid), and other excipients useful in normal animal feed or basal feed, are described throughout the specification and examples.

(d) Physical Form of the Feed Composition

According to various embodiments, the feed composition may be in any suitable form known in the animal feed art, and may be wet or dry. For example, according to certain embodiments, the feed composition may be in a form selected from the group consisting of a complete feed, a feed supplement, a feed additive, a premix, a top-dress, a tub, a mineral, a meal, a block, a pellet, a mash, a liquid supplement, a drench, a bolus, a treat, and combinations of any thereof. Additionally, a feed composition may optionally be ground.

(e) Preparation of the Feed Composition

In various embodiments, the comprising conjugated linoleic acid (CLA) and cyclopropenoid fatty acid (CPFA) may be introduced to the animal feed by way of various methods, depending on whether the feed composition is in a liquid or solid form. Non-limiting examples of introducing the comprising conjugated linoleic acid (CLA) and cyclopropenoid fatty acid (CPFA) to animal feed may be formulating into normal animal feed, top-dressing the solid composition on normal animal feed, spraying the comprising conjugated linoleic acid (CLA) and cyclopropenoid fatty acid (CPFA) onto normal animal feed, or combinations thereof. Basal feed may also be added to the feed composition at any point in the preparation.

(II) Methods for Improving the Growth in Non-Human Animals

Another aspect of the disclosure encompasses methods for improving the growth aspects of non-human animals. The method comprises administering a feed composition supplemented with comprising conjugated linoleic acid (CLA) and cyclopropenoid fatty acid (CPFA) as described in Section (1) at least once per day. Growth aspects in non-human animals, in broad terms, may be defined as an animal which exhibits improved growth after digestion of the feed composition as compared to the control group that has not been administered the feed composition of the present disclosure.

Generally, the average daily intake of the at least one conjugated linoleic acid may range from about 1.0 g/day to about 10.0 g/day for the non-human animal. In various embodiments, the average daily intake of the at least one conjugated linoleic acid may range from 1.0 g/day to about 10.0 g/day, from about 3.0 g/day to about 8.0 g/day, or from about 4.0 g/day to about 7.5 g/day for the non-human animal.

In general, the average daily intake of the at least one cyclopropenoid fatty acid may range from about 0.1 g/day to about 1.0 g/day for the non-human animal. In various embodiments, the average daily intake of the at least one cyclopropenoid fatty acid may range from 0.1 g/day to about 1.0 g/day, from about 0.15 to about 0.7 g/day, or from about 0.2 to about 0.4 g/day for the non-human animal.

In various embodiments, the non-human animal may be of varying age and health. Generally, the non-human animal may be a livestock mammal, an avian species or poultry, aquaculture organisms, or mariculture organisms. The aquaculture organisms or mariculture organisms may be fresh or salt water organisms. Non-limiting example of suitable livestock mammals may be beef cattle, horses, dairy cattle, veal, pigs, goats, sheep, bison, llama, or alpaca. Non-limiting examples of suitable avian species or poultry may be chickens, including broilers, layers, and breeders, ducks, game hens, geese, guinea fowl/hens, quail, and turkeys. Non-limiting species of aquaculture species may be carp, salmon, tilapia, catfish, Bluefin tuna, shrimp, prawns, crawfish, crabs, oysters, mussels, abalone, aquatic reptiles, aquatic amphibians, sea cucumbers, sea urchins, or shell fish.

Preferably, the method comprises oral administration of the feed composition to non-human animals. One or more doses of the feed composition may be administered to non-human animals. As will be appreciated by one of skill in the art, the amount of feed composition orally administered to the non-human animal can and will vary depending on the species of the non-human animal, along with body weight, sex, age and/or medical condition, as well as the particular growth rate and efficiency desired to be achieved.

"Improved growth," as defined herein, refers to a positive change in size and/or maturation over a period of time in the non-human animal. In various embodiments, the non-human animals may exhibit improved growth including for example an increase in average daily weight gain (ADG), an increase in the average daily food intake (ADFI), an improved overall body weight, an increase in food conversion, reduced mortality, reduced health issues, or combinations thereof.

The non-human animals may exhibit an increase in the average daily weight gain (ADG) of at least 1.0% as compared to a control group fed without the feed composition of the present disclosure. In various embodiments, non-human animals may exhibit an increase in the average daily weight gain (ADG) of at least 1.0%, at least 1.25%, at least 1.5%, at least 1.75%, at least 2.0%, at least 2.25%, at least 2.5%, at least 2.75, at least 2.9%, or more as compared to a control group.

The non-human animals may exhibit an increase in the average daily food intake (ADFI) of at least of at least 0.05 lb/day as compared to a control group. In various embodiments, the non-human animals may exhibit an increase in the average daily food intake of at least 0.1 lb/day, at least 0.2 lb/day, at least 0.3 lb/day, at least 0.4 lb/day, at least 0.5 lb/day, at least 0.6 lb/day, at least 0.7 lb/day, at least 0.8 lb/day, at least 0.9 lb/day, of at least 1.0 lb/day, at least 1.2 lb/day, at least 1.5 lb/day, or more as compared to a control group.

Another valuable measure to ascertain growth is the ratio F/G. The ratio F/G is defined as the ADFI/ADG which is termed "feed efficiency." Generally, F/G may range from 2.0 to 3.5. In various embodiments, the F/G may range from about 2.0 to about 3.8, from about 2.3 to about 3.8, or from about 2.8 to about 3.2. As compared to the control group, the ratio F/G may decrease by about 0.5%. In various embodiments, the ratio F/G may decrease by about 0.5%, by about 0.75%, by about 1.0%, by about 1.25%, by about 1.5%, by about 1.75%, by about 2.0%, by about 2.25%, by about 2.5%, by about 2.75%, or more.

The non-human animals may show an improved body weight by at least about 2.0 lbs as compared to a control group. In various embodiments, the percent increase of the improved body weight may be at least about 2.0 lbs, by at least 2.5 lbs, by at least 3.0 lbs, by at least 3.5 lbs, by at least 4.0 lbs, by at least 4.5 lbs, by at least 5.0 lbs, or more.

The non-human animals may show reduced health issues as compared to a control group. "Improved health," as defined herein, refers to a reduction of incidences of diarrhea, reduction in the number of days of diarrhea, a decrease in mortality, a decrease in cytokine panel measuring TNF-alpha, decrease in immunocrit levels, or combinations thereof in the non-human animals as compared to a control group.

(III) Methods for Increasing Carcass Gain and Repartitioning Nutrients to Muscles (Nitrogen Retention) in Non-Human Animals Still another aspect of the disclosure encompasses methods for increasing carcass gain and repartitioning nutrients to muscles in non-human animals. Generally, the method comprises administering the feed composition as described in Section (1) comprising at least one cyclopeniod fatty acid and at least one conjugated linoleic acid to non-human animals at least once per day. As appreciated by the skilled artisan, repartitioning nutrients to muscles in non-human animals is referred to as "nitrogen retention". Nitrogen retention in non-human animals may broadly be defined as a non-animal which exhibits an increase in carcass weight, increased loin depth, increased lean yield; carcass ADG (Average Daily Gain), hot carcass weight feed efficiency, or combinations thereof.

Generally, the average daily intake of the at least one conjugated linoleic acid may range from about 1.0 g/day to about 10.0 g/day for the non-human animal. In various embodiments, the average daily intake of the at least one conjugated linoleic acid may range from 1.0 g/day to about 10.0 g/day, from about 3.0 g/day to about 8.0 g/day, or from about 4.0 g/day to about 7.5 g/day for the non-human animal.

In general, the average daily intake of the at least one cyclopropenoid fatty acid may range from about 0.1 g/day to about 1.0 g/day for the non-human animal. In various embodiments, the average daily intake of the at least one cyclopropenoid fatty acid may range from 0.1 g/day to about 1.0 g/day, from about 0.15 to about 0.7 g/day, or from about 0.2 to about 0.4 g/day for the non-human animal.

In various embodiments, the non-human animal may be of varying age and health. Generally, the non-human animal may be a livestock mammal, an avian species or poultry, aquaculture organisms, or mariculture organisms. The aquaculture organisms or mariculture organisms may be fresh or salt water organisms. Non-limiting example of suitable livestock mammals may be beef cattle, horses, dairy cattle, veal, pigs, goats, sheep, bison, llama, or alpaca. Non-limiting examples of suitable avian species or poultry may be chickens, including broilers, layers, and breeders, ducks, game hens, geese, guinea fowl/hens, quail, and turkeys. Non-limiting species of aquaculture species may be carp, salmon, tilapia, catfish, Bluefin tuna, shrimp, prawns, crawfish, crabs, oysters, mussels, abalone, aquatic reptiles, aquatic amphibians, sea cucumbers, sea urchins, or shell fish.

Preferably, the method comprises administering the feed composition to a non-human animal. One or more doses of the feed composition may be administered to non-human animals per day. As will be appreciated by one of skill in the art, a dose and the number of doses of the feed composition can and will vary depending on the body weight, sex, age and/or medical condition of the non-human animals. The desired attributes for repartitioning of nutrients to muscles in non-human animals can be measured and adjusted to achieve the desired the effect.

In general, the non-human animal may show an increase in hot carcass weight (HCW) of at least about 2.5 lbs as compared to a control group. The hot carcass weight as defined herein refers to the amount of usable meat products obtained after the non-human animal is slaughtered or dressed. In various embodiments, the non-human animal may show an increase in hot carcass weight of at least about 2.5 lbs, at least about 3.0 lbs, at least about 3.5 lbs, at least about 4.0 lbs, at least about 4.5 lbs, at least about 5.0 lbs, at least about 5.5 lbs, at least about 6.0 lbs, or more.

Another useful measurement for the increase in carcass weight is carcass yield. Carcass yield as defined herein refers to the amount of usable meat product obtained after the non-human animal is slaughtered or dressed as compared to the total weight of the non-human animal. The carcass yield in the non-human animal that has been fed the feed composition of the present disclosure can then be compared to the carcass yield of the control group. Generally, the carcass yield of the non-human animal that has been fed the feed composition compared to the control group may be increased by about 0.25%. In various embodiments, the carcass yield of the non-human animal that has been fed the feed composition of the present disclosure compared to the control group may be increased by about 0.25%, by about 0.3%, by about 0.35%, by about 0.4%, by about 0.45%, by about 0.50%, by about 0.55%, by about 0.60%, by about 0.65%, by about 0.7%, by about 0.75%, by about 0.8%, by about 0.85%, by about 0.9%, or more.

In general, the non-human animal that has been fed the feed composition may show an increase in loin depth of at least about 1% as compared to the control group. In various embodiments, the non-human animal fed the feed composition may show an increase in loin depth of at least about 1%, at least about 1.5%, at least about 2%, at least about 2.5%, at least about 3.0%, at least about 3.5%, at least about 4.0%, at least about 4.5%, at least about 5.0%, at least about 5.5%, or more.

In general, the non-human animal fed the feed composition may increase the lean percentage in the non-human animal by at least about 0.25% as compared to the control group. In various embodiments, the non-human animal fed the feed composition may increase the lean percentage in the non-human animal by at least about 0.25%, at least about 0.30%, at least about 0.35%, at least about 0.40%, at least about 0.45%, at least about 0.50%, at least about 0.55%, at least about 0.60%, at least about 0.65%, at least about 0.70%, at least about 0.75%, or more.

Generally, the non-human animal fed the feed composition may show an increase the carcass average daily gain (Carcass ADG). The carcass average daily gain as defined herein refers to the amount of usable meat products obtained after the non-human animal is slaughtered or dressed as compared the average daily gain of the non-human animal before slaughtering or dressing. Generally, the carcass average daily gain may be at least 5% as compared to the control group. In various embodiments, the carcass average daily gain may be at least 5%, at least 6%, at least 7%, at least 8%, at least 9%, or more.

Still another valuable measurement is the hot carcass weight feed efficiency. This value indicates the efficient use of feed of the non-human animal as it relates to the hot carcass weight after the non-human animal is slaughtered or dressed. In general, the carcass hot weight feed efficiency in the non-human animal fed the feed composition may increase by at least 4% as compared to the control group. In various embodiments, the carcass hot weight feed efficiency in the non-human animal may increase by at least 4%, at least 5%, at least 6%, at least 7%, at least 8%, or more.

(IV) Methods for Controlling Iodine Values (IV) in Non-Human Animals Using a Feed Composition Comprising CLA and CPFAs Still another aspect of the disclosure encompasses methods for controlling iodine values in non-human animals. As appreciated by the skilled artisan, iodine value is a measurement to estimate the amount of unsaturation present in the fatty acids present in carcass fat. Increased amounts of unsaturated fatty acids produce "softer" or less firm meat, and therefore iodine value can be used as indicator of overall carcass fat firmness. Higher iodine values indicate the non-human animal, after being slaughtered or dressed, has more fat in the carcass (i.e., a softer carcass) while lower iodine values indicate the non-human animal will exhibit a more firm carcass.

Iodine value can be measured by varying methods known to the skilled artisan. One method calculates the iodine value by the following equation by American Oil Chemist's Society (AOCS) (1998):

Iodine value=[C16:1]×0.95+[C18:1]×0.86+[C18:2]× 1.732+[C18:3]×2.616+[C20:1]×0.785+[C22:1]× 0.723

This approach has been widely used by researchers to determine carcass fat iodine and can be done easily after the fatty acid composition has been determined for a fat deposit. This method provides an approximate iodine value in the non-human animal. Another method comprises direct laboratory analysis that involves iodine binding to unsaturated or double bonds in fatty acids; thus a greater amount of iodine will bind to a sample that has a greater proportion of unsaturated fatty acids (AOCS, 1998). This process is the true chemical analysis procedure for determining iodine value and provides accurate results. Finally, near-infrared analysis (NIR) can be used to determine iodine value. Some meat processors are utilizing this method as it is the most rapid method for determining iodine value results. However, the precise calibration of the near-infrared analysis machine is essential to accurately determine the iodine value of the carcass fat sampled.

The method comprises administering the feed composition of Section (1) comprising at least one cyclopropenoid fatty acid and at least one conjugated linoleic acid to a non-human animal at least once per day. The iodine value in non-human animals may broadly be defined as an animal which exhibits controlled iodine values, where controlled iodine values comprises decreasing the iodine value, increasing the saturated fatty acids, reducing the mono- and polysaturated acid in the fat, decreasing the delta-9 desturase activity, reducing the carcass unsaturated fat content, the melting point of the carcass, carcass hardness, jowl firmness, backfat firmness, stick to belly fat, or combinations thereof.

Generally, the average daily intake of the at least one conjugated linoleic acid may range from about 1.0 g/day to about 10.0 g/day for the non-human animal. In various embodiments, the average daily intake of the at least one conjugated linoleic acid may range from 1.0 g/day to about 10.0 g/day, from about 3.0 g/day to about 8.0 g/day, or from about 4.0 g/day to about 7.5 g/day for the non-human animal.

In general, the average daily intake of the at least one cyclopropenoid fatty acid may range from about 0.1 g/day to about 1.0 g/day for the non-human animal. In various embodiments, the average daily intake of the at least one cyclopropenoid fatty acid may range from 0.1 g/day to about 1.0 g/day, from about 0.15 to about 0.7 g/day, or from about 0.2 to about 0.4 g/day for the non-human animal.

In various embodiments, the non-human animal may be of varying age and health. Generally, the non-human animal may be a livestock mammal, an avian species or poultry, aquaculture organisms, or mariculture organisms. The aquaculture organisms or mariculture organisms may be fresh or salt water organisms. Non-limiting example of suitable livestock mammals may be beef cattle, horses, dairy cattle, veal, pigs, goats, sheep, bison, llama, or alpaca. Non-limiting examples of suitable avian species or poultry may be chickens, including broilers, layers, and breeders, ducks, game hens, geese, guinea fowl/hens, quail, and turkeys. Non-limiting species of aquaculture species may be carp, salmon, tilapia, catfish, Bluefin tuna, shrimp, prawns, crawfish, crabs, oysters, mussels, abalone, aquatic reptiles, aquatic amphibians, sea cucumbers, sea urchins, or shell fish.

The iodine value derived using the equation shown above provides an expected drop in the iodine value. Generally, the expected drop in the iodine value in the non-human animal may range from about −3.5 to about −4.5 when administered the feed composition in Section (1) as compared to the control group. In various embodiments, the expected drop in iodine value of the non-human animal may be about −3.5, about −3.6, about −3.7, about −3.8, about −3.9, about −4.0, about −4.1, about −4.2, about −4.3, about −4.4 or about −5.5.

In general, the actual iodine value of the non-human animal after administration of the feed composition in Section (1) comprising at least one cyclopropenoid fatty acid and at least one conjugated linoleic acid may range from about 71.5 to about 72.5. In various embodiments, the actual iodine value of the non-human animal after administration of the feed composition in Section (1) may range from about 71.5 to about 72.5, from about 71.6 to about 72.3, from about 71.7 to about 72.2, or from about 71.8 to about 72.0.

Another useful indicator is the actual iodine value derived through lab experiments divided by the expected iodine value calculated using the above equation as a percentage. A higher percentage in this value would demonstrate the synergistic effect of the feed composition described above in Section (1) comprising at least one cyclopropenoid fatty acid and at least one conjugated linoleic acid on the iodine value. Generally, the percentage of the actual iodine value divided by the expected iodine value may range from about 101% to about 140%. In various embodiments, the percentage of the actual iodine value divided by the expected iodine value may range from about 101% to about 140%, from about 110% to about 135%, from about 115% to about 132%, or from about 120% to about 130%. In an embodiment, the percentage of the actual iodine value divided by the expected iodine value may range from about 118% to about 125%.

In general, the non-human animal fed the feed composition may exhibit a decrease in percentage difference of iodine values from about −0.01% to about −10% as compared to the control group not fed the feed composition. A decrease in the iodine value indicates the overall carcass is more firm. In various embodiments, the percentage difference in the iodine value may range from about −0.01% to about −10%, from about −1% to about −9%, from about −2% to about −8%, from about −3% to about −7%, or from −4% to about −6%.

Iodine Value Potential (IVP) of the feed is a method for assessing the impact of increasing unsaturated fat content of the feed and its impact on potential IV of the carcass or the non-human animal. A typical corn soybean meal diet without added fat has an iodine value potential (IVP) of 46, suggesting that the carcass firmness will be acceptable as ingredients in the diet do not negatively affect the carcass fat. Adding saturated fat sources (e.g., beef tallow) to the diets (5% inclusion rate) will increase the IVP to approximately 70-75, which will still result in an acceptable carcass quality. However, if diets are formulated to contain 40% plus DDGS or include 5% corn oil, the IVP of the diet increases to 90 and 120, respectively. Diets formulated to these high levels of IVP will result in an unacceptable meat quality of the non-human animal. Administration of the feed composition with oils comprising CPFA and CLA increases the IVP 2 to 10 points. This increase in IVP would be expected to result in a higher IV in the animal. However, the feed composition actually offsets the higher IVP of the diet and reverses the negative impact of the diet formulation.

(V) Methods for Increasing Carcass Gain and Repartitioning Nutrients to Muscles (Nitrogen Retention) in Non-Human Animals Using a Feed Composition Comprising at Least One CPFAs Still another aspect of the disclosure encompasses methods for increasing carcass gain and repartitioning nutrients to muscles in non-human animals. As appreciated by the skilled artisan, the repartitioning of nutrients to muscles in non-human animals is referred to as nitrogen retention. The method comprises administering a feed composition consisting of at least one cyclopropenoid fatty acid and optional additives to non-human animals at least once per day.

In general, the average daily intake of the at least one cyclopropenoid fatty acid may range from about 0.5 g/day to about 1.5 g/day for the non-human animal. In various embodiments, the average daily intake of the at least one cyclopropenoid fatty acid may range from 0.5 g/day to about 1.5 g/day, from about 0.7 to about 1.3 g/day, or from about 0.9 to about 1.1 g/day for the non-human animal.

In various embodiments, the non-human animal may be of varying age and health. Generally, the non-human animal may be a livestock mammal, an avian species or poultry, aquaculture organisms, or mariculture organisms. The aquaculture organisms or mariculture organisms may be fresh or salt water organisms. Non-limiting example of suitable livestock mammals may be beef cattle, horses, dairy cattle, veal, pigs, goats, sheep, bison, llama, or alpaca. Non-limiting examples of suitable avian species or poultry may be chickens, including broilers, layers, and breeders, ducks, game hens, geese, guinea fowl/hens, quail, and turkeys. Non-limiting species of aquaculture species may be carp, salmon, tilapia, catfish, Bluefin tuna, shrimp, prawns, crawfish, crabs, oysters, mussels, abalone, aquatic reptiles, aquatic amphibians, sea cucumbers, sea urchins, or shell fish.

Preferably, the method for increasing carcass gain and repartitioning nutrients to muscles in non-human animals comprises administration of a feed composition at least one cyclopropenoid fatty acids and normal animal feed or basal feed to a non-human animal. One or more doses of the feed composition may be administered to a non-human animal per day. As will be appreciated by one of skill in the art, a dose and the number of doses of the feed composition can and will vary depending on the body weight, sex, age and/or medical condition of the non-human animals. The desired increase in carcass gain and repartitioning of nutrients to muscles in non-human animals can be measured and adjusted to achieve the desired the effect.

In general, the non-human animal may show an increase in hot carcass weight (HCW) of at least about 2.5 lbs as compared to the control group not fed the feed composition. The hot carcass weight as defined herein refers to the amount of usable meat products obtained after the non-human animal is slaughtered or dressed. In various embodiments, the non-human animal may show an increase in hot carcass weight of at least about 2.5 lbs, at least about 3.0 lbs, at least about 3.5 lbs, at least about 4.0 lbs, at least about 4.5 lbs, at least about 5.0 lbs, at least about 5.5 lbs, at least about 6.0 lbs, or more.

Another useful measurement for the increase in carcass weight is carcass yield. The carcass yield as defined herein refers to the amount of usable meat products obtained after the non-human animal is slaughtered or dressed as compared to the total weight of the non-human animal. The carcass yield in the non-human animal being administered feed composition can then be compared to the carcass yield of the control group. Generally, the carcass yield of the non-human animal being administered the feed composition compared to the control group may increase by about 0.25%, In various embodiments, the carcass yield of the non-human animal being administered the feed composition compared to the control group not administered may increase by about 0.25%, by about 0.3%, by about 0.35%, by about 0.4%, by about 0.45%, by about 0.50%, by about 0.55%, by about 0.60%, by about 0.65%, by about 0.7%, by about 0.75%, by about 0.8%, by about 0.85%, by about 0.9%, or more.

In general, the non-human animal being administered the feed composition may show an increase in loin depth of at least about 1% as compared to the control group. In various embodiments, the non-human animal being administered the feed composition may show an increase in loin depth of at least about 1%, at least about 1.5%, at least about 2%, at least about 2.5%, at least about 3.0%, at least about 3.5%, at least about 4.0%, at least about 4.5%, at least about 5.0%, at least about 5.5%, or more.

The iodine value derived using the equation, as shown above in Section (IV), provides an expected drop in the iodine value. Generally, the expected drop in the iodine value in the non-human animal may range from about −4.4 to about −6.0. In various embodiments, the actual iodine value derived from direct laboratory analysis may be about −4.4, about −4.5, about −4.6, about −4.7, about −4.8, about −4.9, about −5.0, about −5.1, about −5.2, about −5.3, about −5.4, about −5.5, about −5.6, about −5.7, about −5.8, about −5.9, or about −6.0.

In general, the actual iodine value of the non-human animal after administration of the feed composition in Section (1) may range from about 70.5 to about 71.5. In various embodiments, the actual iodine value of the non-human animal after administration of the feed composition in Section (1) may range from about 70.5 to about 71.5, from about 70.6 to about 71.4, from about 70.7 to about 71.3, from about 70.8 to about 71.2, or from about 70.9 to about 71.1.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1

A testing protocol of the average daily intake of cyclopropenoid fatty acids (CPFAs) and conjugated linoleic acid (CLA) and the cyclopropenoid fatty acids (CPFAs) was set up to test the effects on growth performance and carcass quality in finishing pigs. Table 1 below shows the broad ranges and more preferred ranges which were evaluated.

| Additive | Ranges | Range Description |
|---|---|---|
| CPFAs in CPFA and CLA | 0.1 to 1.0 g/day | Broad Ranges |
| | 0.15 to 0.7 g/day | More Preferred Range |
| | 0.2 to 0.4 g/day | Most Preferred Range |
| CLA in CPFA and CLA | 1.0 to 10.0 g/day | Broad Range |
| | 3.0 to 8.0 g/day | More Preferred Range |
| | 4.0 to 7.5 g/day | Most Preferred Range |
| CPFA alone | 0.5 to 1.5 g/day | Broad Range |
| | 0.7 to 1.3 g/day | More Preferred Range |
| | 0.9 to 1.1 g/day | Most Preferred Range |

A total of 1,238 mixed sex late finishing pigs with average BW of ~190-200 lbs were used to determine the potential synergistic effects of cyclopropenoid fatty acids (CPFAs) and conjugated linoleic acid (CLA) on growth performance and carcass quality in finishing pigs. On the first day of the experiment, pigs were weighed by pen. Pen weights were used to block pigs by body weight, and pens within block were randomly assigned to one of 4 dietary treatments (Table 2) in a randomized complete block design. The design resulted in 11 pens for the control treatment and 12 pens per all other treatments.

TABLE 2

Treatment Layout

| Treatment # | Additive | Inclusion Rate | # of Pens | # Pigs/pen | # of Animals |
|---|---|---|---|---|---|
| 1 - Neg Contr | None | XX | 11 | 25-27 | 275-297 |
| 2 - Pos Contr | CPFA | 306 gram/ton | 12 | 25-27 | 300-324 |
| 3 - CPFA − CLA1 | CPFA + CLA | 122 gram/ton CPFAs + 3.36 lb/ton CLA | 12 | 25-27 | 300-324 |
| 4 - CPFA − CLA2 | CPFA + CLA | 92 gram/ton CPFAs + 5.04 lb/ton CLA | 12 | 25-27 | 300-324 |
| | | | | Total | 1,269 |

Experimental diets (Table 3) were formulated to be isocaloric and comparable in amino acid density. The oils used as sources of CPFAs and CLA replaced tallow on a pound per pound basis to assure isocaloric formulations. All diets contained 800 lbs of distillers dried grains (DDGS) as a source of unsaturated fat to increase the iodine value product of the diet, which should result in a softer carcass at harvest and Treatment 3 would increase IVP of the diet by an additional 6 points.

TABLE 3

Diets for Treatments 1-4.

| Item | Trt 1 | Trt 2 | Trt 3 | Trt 4 |
|---|---|---|---|---|
| Ingredient, lb | 215-250 | 215-250 | 215-250 | 215-250 |
| Corn - Fine Ground | 1075.40 | 1075.40 | 1075.40 | 1075.40 |
| Aurora DDGS | 800.00 | 800.00 | 800.00 | 800.00 |
| Salt | 12.00 | 12.00 | 12.00 | 12.00 |
| Calcium Carbonate 38% | 20.94 | 20.94 | 20.94 | 20.94 |
| Fat -- tallow | 78.39 | 73.39 | 70.39 | 67.89 |
| AA-L-Lysine HCL 78.8% | 9.49 | 9.49 | 9.49 | 9.49 |
| AA-Threonine | 0.45 | 0.45 | 0.45 | 0.45 |
| AA-Tryptophan 100% | 0.68 | 0.68 | 0.68 | 0.68 |
| PEG GF 2# PMX | 1.80 | 1.80 | 1.80 | 1.80 |
| PHY12 Optip D2000 M | 0.35 | 0.35 | 0.35 | 0.35 |
| Tribasic Copper Chloride | 0.50 | 0.50 | 0.50 | 0.50 |
| CPFA Source | — | 5.00 | 2.00 | 1.50 |
| CLA Source | | | 6.00 | 9.00 |
| Total | 2,000.00 | 2,000.00 | 2,000.00 | 2,000.00 |
| Nutrient Composition | | | | |
| Crude Protein, % | 15.09 | 15.09 | 15.09 | 15.09 |
| Fat, % | 8.57 | 8.57 | 8.57 | 8.57 |
| SW NE, kcal/kg | 2,441.27 | 2,441.27 | 2,441.27 | 2,441.27 |
| Lysine, % | 0.81 | 0.81 | 0.81 | 0.81 |
| SW SI dig Lys, % | 0.69 | 0.69 | 0.69 | 0.69 |
| Calcium, % | 0.43 | 0.43 | 0.43 | 0.43 |
| Phosphorus, % | 0.44 | 0.44 | 0.44 | 0.44 |
| Ca/P Ratio, ratio | 0.97 | 0.97 | 0.97 | 0.97 |
| SW dig P, % | 0.37 | 0.37 | 0.37 | 0.37 |

Pigs were weighed on day 0, 14 and 35, and feed disappearance was collected daily to determine average daily gain, average daily feed intake and feed conversion by treatment. At the end of the study a representative group of pigs (approximately 85 per treatment) were shipped to a commercial packing plant to harvest the carcasses and determine the impact of experimental treatments on pork quality. The following data was collected on the carcass at harvest: hot carcass weight, back fat depth, loin depth, percent lean, gender, and iodine value (IV). Iodine value is used to access the degree of fat saturation in the carcass or an indication of carcass firmness/softness. Twenty-four hours post-harvest, 25 loins each were taken by treatment to determine subjective color, marbling, firmness, Minolta L*, a*, b*, and pH.

Treatment 3 pigs had a 6.2% reduction in carcass iodine value (Table 4). By feeding pigs a combination of CPFA (122 gram/ton) and CLA (3.36 lb/ton), the carcass iodine value was reduced by 5.1%, statistically similar as feeding pig's 306 gram/ton CPFA. Although carcass fat firmness was improved as indicated by the reduction in iodine value, muscle firmness, color and pH was not influenced by these dietary manipulations.

TABLE 4

Effect of CPFA and CLA on Carcass Firmness

| Item | Control | 306 grams CPFA | 122 grams CPFA 3.36 lb CLA | 92 grams CPFA 5.04 lb CLA | PSE | P-value |
|---|---|---|---|---|---|---|
| # of Pens | 11 | 12 | 12 | 12 | | |
| # of Pigs | 286 | 314 | 317 | 316 | | |
| Intake of CPFA, g/day | 0.00 | 1.01 | 0.392 | 0.293 | | |
| Intake of CLA, g/day | 0.00 | 0.00 | 4.87 | 7.30 | | |
| Total intake of CPFA, g | 0.0 | 36.22 | 14.08 | 10.58 | | |
| Total intake of CLA, g | 0.0 | 0.0 | 175.17 | 262.64 | | |
| IV | $75.7^a$ | $71.0^c$ | $71.9^{bc}$ | $72.2^b$ | 0.4 | <.0001 |
| IV Change over Control | | −4.66 | −3.85 | −3.46 | | |
| Loin measurements | | | | | | |
| # of Pigs | 25 | 25 | 25 | 25 | | |
| Color score | 3.30 | 3.50 | 3.40 | 3.28 | 0.11 | 0.45 |
| Marbling score | 2.29 | 2.49 | 2.35 | 2.65 | 0.17 | 0.40 |
| Firmness score | 2.17 | 2.42 | 2.26 | 2.51 | 0.16 | 0.37 |
| PH | 5.63 | 5.70 | 5.67 | 5.66 | 0.03 | 0.33 |
| Minolta L* | 47.3 | 46.0 | 46.6 | 46.9 | 0.5 | 0.39 |
| Minolta a* | 8.58 | 8.48 | 8.58 | 8.72 | 0.23 | 0.90 |
| Minolta b* | −1.68 | −1.78 | −1.72 | −1.68 | 0.15 | 0.96 |

$a, b, c$ Means without a common superscript differ (P < 0.05)
$x, y$ Means without a common superscript tend to differ (P < 0.10)

Both CPFA and CLA have been shown to reduce the iodine value of pork fat and improve the firmness of the carcass. The data from the current study illustrates that 306 gram of CPFA oil significantly reduce the IV (Table 4) which is consistent with the work from Hagen (2016). The data in Table 5 illustrates the changes in carcass IV when combining CPFA and CLA together. By using the IV change in pigs fed CPFA solely, the data indicated that it required 7.70 g per 1 point change in IV in the carcass (Table 5). The data in the literature suggests that it requires 240 g of an oil containing 56% CLA to reduce the carcass IV by 1 point. Thus, the expected change in IV for pigs fed a blend of 122 gram CPFA and 3.36 lb of CLA/ton (1:12.5 ratio) was calculated as a 3.1 point reduction in carcass IV. However, the actual result was a 3.9 point reduction or a 26% greater reduction in carcass IV than the expected impact calculated for the two individual oil components. However, by further increasing the CLA component and reducing the CPFA component, the expected improvement no longer showed a synergistic effect as the reduction in IV was near expectation at 97% of the expected effect.

TABLE 5

Synergy of Combining CPFA and CLA to Reduce Carcass Iodine Value (IV)

| Item | 306 gram CPFA | 122 gram CPFA 3.36 lb CLA | 92 gram CPFA 5.04 lb CLA |
|---|---|---|---|
| Expected IV drop from CPFA | | −1.8 | −1.4 |
| Expected IV drop from CLA | | −1.3 | −2.0 |
| Total expected IV drop | −4.7 | −3.1 | −3.4 |
| Actual IV drop | −4.7 | −3.9 | −3.5 |
| Actual: Expected, % | 100% | 126% | 97% |

Body weight gain was not impacted by any of the treatments in the experiment (Table 6). Although adding CPFA to the diet didn't demonstrate to change feed conversion in a meaningful manner, the addition of CLA to CPFA improved feed conversion with increased inclusion rates of CLA to the diet. These changes may be a result of lower average daily feed intake while maintain a similar growth rate. The data further illustrate an increase in carcass leanness as illustrated by increased loin depth and an improvement in lean yield in the carcass. In both cases the lean values were enhanced by the combination of CPFA and CLA.

TABLE 6

Effect of CPFA and CLA on Growth Performance and Carcass Yield

| Item | Control | 306 gram CPFA | 122 gram CPFA + 3.36 lb CLA | 92 gram CPFA + 5.04 lb CLA | PSE | P-value |
|---|---|---|---|---|---|---|
| # of Pens | 11 | 12 | 12 | 12 | | |
| # of Pigs | 286 | 314 | 317 | 316 | | |
| Start BW, lb | 210.6 | 211.3 | 210.5 | 209.9 | 2.3 | 0.98 |
| Growth performance Week 1-2; 14 days | | | | | | |
| ADG, lb/day | 2.33$^a$ | 2.26$^{ab}$ | 2.19$^b$ | 2.20$^b$ | 0.03 | 0.02 |
| ADFI, lb/day | 6.47$^a$ | 6.34$^{ab}$ | 6.20$^b$ | 6.22$^b$ | 0.07 | 0.03 |
| F/G | 2.78 | 2.81 | 2.83 | 2.83 | 0.04 | 0.76 |
| BW end of Week 3, lb | 243.2$^a$ | 242.2$^{ab}$ | 241.3$^b$ | 241.5$^b$ | 0.5 | 0.03 |
| Week 3-5; 22 days | | | | | | |
| ADG, lb/day | 1.97 | 2.05 | 2.01 | 2.01 | 0.04 | 0.54 |
| ADFI, lb/day | 6.59 | 6.75 | 6.52 | 6.50 | 0.08 | 0.14 |
| F/G | 3.35 | 3.30 | 3.25 | 3.24 | 0.04 | 0.25 |
| BW end of Week 6, lb | 281.9 | 282.1 | 280.3 | 280.7 | 1.0 | 0.52 |
| Overall; Week 1-5; 36 days | | | | | | |
| ADG, lb/day | 2.12 | 2.14 | 2.09 | 2.09 | 0.03 | 0.48 |
| ADFI, lb/day | 6.54 | 6.57 | 6.39 | 6.38 | 0.07 | 0.10 |
| F/G | 3.09 | 3.08 | 3.06 | 3.05 | 0.03 | 0.81 |
| Removal, % | 0.70$^{ab}$ | 1.27$^a$ | 0.00$^b$ | 0.95$^a$ | | 0.28 |
| Carcass characteristics | | | | | | |
| # of Pigs | 63 | 102 | 79 | 75 | | |
| Live weight, lb | 281.2 | 284.8 | 279.4 | 285.7 | | |
| HCW, lb | 213.8 | 216.6 | 211.6 | 214.1 | 2.4 | 0.31 |
| Yield, % | 76.0 | 76.1 | 75.7 | 75.0 | | 1.00 |
| Backfat thickness, mm | 13.7 | 13.9 | 13.8 | 13.4 | 0.3 | 0.63 |
| Loin depth, mm | 61.9$^x$ | 64.0$^y$ | 65.0$^y$ | 64.7$^y$ | 0.9 | 0.06 |
| Lean, % | 58.0 | 58.1 | 58.3 | 58.5 | 0.2 | 0.30 |
| IV | 75.7$^a$ | 71.0$^c$ | 71.9$^{bc}$ | 72.2$^b$ | 0.4 | <.0001 |
| IV change over Control | | −4.66 | −3.85 | −3.46 | | |
| Loin measurements | | | | | | |
| # of Pigs | 25 | 25 | 25 | 25 | | |
| Color score | 3.30 | 3.50 | 3.40 | 3.28 | 0.11 | 0.45 |
| Marbling score | 2.29 | 2.49 | 2.35 | 2.65 | 0.17 | 0.40 |
| Firmness score | 2.17 | 2.42 | 2.26 | 2.51 | 0.16 | 0.37 |
| PH | 5.63 | 5.70 | 5.67 | 5.66 | 0.03 | 0.33 |
| Minolta L* | 47.3 | 46.0 | 46.6 | 46.9 | 0.5 | 0.39 |
| Minolta a* | 8.58 | 8.48 | 8.58 | 8.72 | 0.23 | 0.90 |
| Minolta b* | −1.68 | −1.78 | −1.72 | −1.68 | 0.15 | 0.96 |

$^{a, b, c}$Means without a common superscript differ (P < 0.05)

$^{x, y}$Means without a common superscript tend to differ (P < 0.10)

Example 2

A total of 1,238 mixed sex late finishing pigs with average BW of ~190-200 lb were used to determine the potential synergistic effects of cyclopropenoic fatty acids (CPFAs) and conjugated linoleic acid (CLA) on growth performance and carcass quality in finishing pigs. On the first day of the experiment, pigs were weighed by pen. Pen weights were used to block pigs by body weight, and pens within block were randomly assigned to one of 4 dietary treatments (Table 7) in a randomized complete block design. The design resulted in 11 pens for the control treatment and 12 pens per all other treatments.

TABLE 7

Treatment Layout

| Treatment # | Additive | Inclusion Rate Product | # Pigs/pen | # of Animals | Micro-tracer[2] |
|---|---|---|---|---|---|
| 1 - Neg Control | None | XX | 25-27 | 275-297 | Violet |
| 2 - Pos Control | CPFA | 306 gram/ton | 25-27 | 300-324 | Red |
| 3 - CPFA – CLA6 | CPFA + CLA 1 | 122 gram/ton CPFA + 3.36 lb/ton CLA | 25-27 | 300-324 | Blue |
| 4 - CPFA – CLA9 | CPFA + CLA 2 | 122 gram/ton CPFA + 5.04 lb/ton CLA | 25-27 | 300-324 | Orange |
| | | Total | | 1,269 | |

Experimental diets (Table 8) were formulated to be isocaloric and comparable in amino acid density. The oils used as sources of CPFAs and CLA replaced tallow on a pound per pound basis to assure isocaloric formulations. All diets contained 800 lbs of distillers dried grains (DDGS) as a source of unsaturated fat to increase the iodine value potential of the diet, which should result in a softer carcass at harvest.

TABLE 8

Diets for Treatments[1].

| Item | Control | CPFA | CPFA + CLA 1 | CPFA + CLA 2 |
|---|---|---|---|---|
| Ingredient, lb | | | | |
| Corn - Fine Ground | 1075.40 | 1075.40 | 1075.40 | 1075.40 |
| Aurora DDGS | 800.00 | 800.00 | 800.00 | 800.00 |
| Salt | 12.00 | 12.00 | 12.00 | 12.00 |
| Calcium Carbonate 38% | 20.94 | 20.94 | 20.94 | 20.94 |
| Fat - tallow | 78.39 | 73.39 | 70.39 | 67.39 |
| AA-L-Lysine HCL 78.8% | 9.49 | 9.49 | 9.49 | 9.49 |
| AA-Threonine | 0.45 | 0.45 | 0.45 | 0.45 |
| AA-Tryptophan 100% | 0.68 | 0.68 | 0.68 | 0.68 |
| PEG GF 2# PMX (2000#TOTE) | 1.80 | 1.80 | 1.80 | 1.80 |
| PHY12 Optip D2000 M | 0.35 | 0.35 | 0.35 | 0.35 |
| Tribasic Copper Chloride | 0.50 | 0.50 | 0.50 | 0.50 |
| LIPINATE | — | 5.00 | 2.00 | 2.00 |
| Experimental CLA | | | 6.00 | 9.00 |
| Total | 2,000.00 | 2,000.00 | 2,000.00 | 2,000.00 |
| Nutrient Composition | | | | |
| Crude Protein, % | 15.09 | 15.09 | 15.09 | 15.09 |
| Fat, % | 8.57 | 8.57 | 8.57 | 8.57 |
| SW NE, kcal/kg | 2,441.27 | 2,441.27 | 2,441.27 | 2,441.27 |
| Lysine, % | 0.81 | 0.81 | 0.81 | 0.81 |
| SW SI dig Lys, % | 0.69 | 0.69 | 0.69 | 0.69 |
| Mean Diam, microns | 268.85 | 268.85 | 268.85 | 268.85 |
| Calcium, % | 0.43 | 0.43 | 0.43 | 0.43 |
| Phosphorus, % | 0.44 | 0.44 | 0.44 | 0.44 |
| Ca/P Ratio, ratio | 0.97 | 0.97 | 0.97 | 0.97 |
| SW dig P, % | 0.37 | 0.37 | 0.37 | 0.37 |

[1]Only one ration was fed throughout the length of this trial.

Pigs were weighed on day 0, 14, 28, and 49 whereas feed disappearance was collected daily to determine average daily gain, average daily feed intake and feed conversion by treatment. At the end of the study a representative group of pigs (approximately 25 per treatment) was shipped to a commercial packing plant to harvest the carcasses and determine the impact of experimental treatments on park quality. The following data was collected on the carcass at harvest: hot carcass weight, carcass yield, back fat depth, loin depth, percent lean, and iodine value. Iodine value was used to access the degree of fat saturation in the carcass or an indication of carcass firmness/softness As in Example 1, the inclusion of CPFAs and a combination of CPFAs and CLA reduced the iodine value of the carcass (Table 9). The combination of CPFA with CLA actually improved iodine value by 18 to 21% more than what was expected from using the products individually. This increase in efficacy suggests that a synergistic effect exists between the two products. Additionally, carcass weight shows a similar synergistic effect in that the combination of the two oils further improved carcass weight gain suggesting a repartitioning effect of feed CPFA and CLA together.

Averaged daily gain was improved by 2.9% and feed conversion improved by 1.8% for pigs fed CPFA+CLA1 compared to pigs fed the control diets. CPFAs alone increased ADG by 1.9% compared to the control fed pigs, whereas CPFA+CLA increased ADG by 2.9%. Feed conversion was markedly improved (−1.8%) compared to the controls vs CFPA alone which reduced feed conversion by less than 1%. This synergistic effect on improved nutrient utilization is further illustrated by a 8.3% reduction in blood urea nitrogen suggesting improved nitrogen retention. Additionally, hot carcass weight was increased in the pigs fed CPFA+CLA compared to the controls by 5.1 lbs. Loin depth was further increased by feeding the CPFA+CLA compared to the CPFA combination alone.

TABLE 9

Effect of CPFA + CLA Blends on Performance and Carcass Traits

| Item | Control | CPFA | CPFA + CLA 1 | CPFA + CLA 2 | PSE | P-value (Overall) | P-value (Con vs. Blend 1) | Blend 1 vs. Control |
|---|---|---|---|---|---|---|---|---|
| # of Pens | 11 | 12 | 12 | 12 | | | | |
| # of Pigs | 293 | 311 | 315 | 314 | | | | |
| Start BW, lb | 185.0 | 185.0 | 184.9 | 184.9 | 2.5 | 1.00 | 0.98 | |
| Growth performance | | | | | | | | |

TABLE 9-continued

Effect of CPFA + CLA Blends on Performance and Carcass Traits

| Item | Control | CPFA | CPFA + CLA 1 | CPFA + CLA 2 | PSE | P-value (Overall) | P-value (Con vs. Blend 1) | Blend 1 vs. Control |
|---|---|---|---|---|---|---|---|---|
| Week 1-2 | | | | | | | | |
| ADG, lb/day | $2.16^{xy}$ | $2.09^x$ | $2.30^y$ | $2.11^x$ | 0.06 | 0.05 | 0.16 | 6.5% |
| ADFI, lb/day | $6.27^x$ | $6.23^{xy}$ | $6.15^{xy}$ | $5.98^y$ | 0.09 | 0.10 | 0.41 | |
| F/G | $2.91^a$ | $2.99^a$ | $2.69^b$ | $2.85^{ab}$ | 0.05 | 0.001 | 0.006 | -7.7% |
| BW end of Week 2, lb | $213.2^x$ | $212.2^x$ | $214.9^y$ | $212.5^{xy}$ | 0.8 | 0.06 | 0.19 | +1.7 lb |
| Week 3-4 | | | | | | | | |
| ADG, lb/day | $2.07^a$ | $2.21^b$ | $2.16^{ab}$ | $2.12^a$ | 0.04 | 0.08 | 0.13 | 4.5% |
| ADFI, lb/day | 6.25 | 6.41 | 6.41 | 6.40 | 0.08 | 0.39 | 0.16 | |
| F/G | $3.03^x$ | $2.91^y$ | $2.98^{xy}$ | $3.02^x$ | 0.04 | 0.05 | 0.28 | -1.9% |
| BW end of Week 4, lb | 248.2 | 250.0 | 251.4 | 248.4 | 1.1 | 0.11 | 0.06 | +3.2 lb |
| Week 1-4 (prior to topping) | | | | | | | | |
| ADG, lb/day | 2.10 | 2.15 | 2.22 | 2.11 | 0.04 | 0.11 | 0.05 | 5.4% |
| ADFI, lb/day | 6.26 | 6.33 | 6.30 | 6.22 | 0.07 | 0.63 | 0.67 | |
| F/G | $2.98^a$ | $2.94^a$ | $2.85^b$ | $2.95^a$ | 0.03 | 0.009 | 0.004 | -4.4% |
| Week 5-7 (after topping) | | | | | | | | |
| ADG, lb/day | 2.06 | 2.09 | 2.03 | 2.03 | 0.03 | 0.49 | 0.54 | -1.5% |
| ADFI, lb/day | 6.78 | 6.90 | 6.85 | 6.79 | 0.07 | 0.55 | 0.29 | |
| F/G | 3.31 | 3.30 | 3.39 | 3.34 | 0.07 | 0.79 | 0.43 | 2.3% |
| BW end of Week 7, lb | $287.4^a$ | $291.2^b$ | $291.9^b$ | $287.3^a$ | 1.1 | 0.005 | 0.01 | +4.5 lb |
| Week 1-7; overall | | | | | | | | |
| ADG, lb/day | 2.09 | 2.13 | 2.15 | 2.08 | 0.02 | 0.12 | 0.08 | 2.9% |
| ADFI, lb/day | 6.45 | 6.54 | 6.50 | 6.43 | 0.06 | 0.54 | 0.47 | |
| F/G | 3.08 | 3.07 | 3.03 | 3.09 | 0.03 | 0.31 | 0.11 | -1.8% |
| Removal, % | 7.2 | 8.4 | 7.3 | 6.7 | | 0.89 | 0.95 | |
| Carcass characteristics | | | | | | | | |
| HCW, lb | $209.4^a$ | $214.7^b$ | $214.5^b$ | $210.0^a$ | 1.0 | 0.0001 | 0.0009 | +5.1 lb |
| Carcass yield, % | $72.9^a$ | $73.7^b$ | $73.5^{ab}$ | $73.1^{ab}$ | 0.2 | 0.04 | 0.02 | +0.6% point |
| Backfat thickness, mm | 16.1 | 16.7 | 15.9 | 16.6 | 0.3 | 0.27 | 0.69 | |
| Loin depth, mm | $67.6^a$ | $69.4^{ab}$ | $70.2^b$ | $70.0^b$ | 0.6 | 0.02 | 0.003 | |
| Lean, % | 57.2 | 57.0 | 57.6 | 57.1 | 0.2 | 0.23 | 0.13 | |
| Carcass ADG | $1.45^a$ | $1.56^b$ | $1.55^b$ | $1.46^{ab}$ | 0.02 | 0.0001 | | |
| Carcass HCW feed efficiency | $4.37^a$ | $4.20^b$ | $4.17^b$ | $4.39^{ab}$ | 0.05 | 0.02 | | |
| IV Measurement | | | | | | | | |
| # of Samples | 26 | 26 | 25 | 23 | | | | |
| IV | $71.8^a$ | $66.5^b$ | $67.0^b$ | $65.9^b$ | 0.6 | <.0001 | <.0001 | |
| CV of IV, % | 3.7 | 3.8 | 4.0 | 5.1 | N/A | 0.92 | 0.98 | |
| Blood metabolites at Wk 6 | | | | | | | | |
| NEFA, μM | 98.2 | | 80.0 | | 17.5 | | 0.30 | |
| BUN, mg/dL | 16.7 | | 15.3 | | 0.8 | | 0.21 | |
| Week 1-7; overall - Adjusted for end BW | | | | | | | | |
| ADG, lb/day | 2.10 | 2.12 | 2.13 | 2.09 | 0.02 | 0.39 | 0.20 | 1.8% |
| ADFI, lb/day | 6.51 | 6.50 | 6.44 | 6.49 | 0.05 | 0.74 | 0.31 | |
| F/G | 3.10 | 3.06 | 3.02 | 3.10 | 0.03 | 0.12 | 0.07 | -2.8% |
| Total expected IV drop | | 5.34 | 4.05 | 4.94 | | | | |
| IV drop over Control | N/A | 5.34 | 4.79 | 5.97 | | | | |
| % change vs expected | | 100% | 118% | 121% | | | | |
| ADFI, lb/day | 6.45 | 6.54 | 6.50 | 6.43 | | | | |

$^{a,\,b}$Means without a common superscript differ (P < 0.05)

$^{x,\,y}$Means without a common superscript tend to differ (P < 0.10)

Example 3

Twenty pigs were used to demonstrate the synergistic effects of feeding CPFA+CLA in combination compared to pigs fed CPFA or CLA alone. Pigs fed 6.72 lbs/ton CLA (Table 10) illustrated improvements in feed conversion, whereas feeding CPFA (306 gram/ton) did not improve feed conversion. The combination of CPFA+CLA resulted in a 19% improvement in feed conversion whereas pigs fed CPFA solely resulted in a 9% improvement in feed conversion and pigs fed CLA resulted in a 13% improvement. Delta 9 desaturase activity was improved similarly between all treatments leading to a similar reduction in carcass iodine value. These data indicated that nutrients are preferentially used for carcass gain, resulting in improved performance and a synergistic effect compared to the CPFA or CLA fed by them.

TABLE 10

Effect of fatty acids on growth performance and carcass quality in finishing pigs

| Item | Control | CPFA | CLA | CPFA + CLA1 | CPFA + CLA2 | PSE | P-value |
|---|---|---|---|---|---|---|---|
| Week 1-3 | | | | | | | |
| ADG, lb/day | 2.00 | 2.60 | 2.80 | 2.53 | 2.69 | 0.26 | 0.22 |
| ADFI, lb/day | 7.16 | 7.83 | 8.00 | 7.20 | 7.67 | 0.48 | 0.71 |
| F:G | $3.66^x$ | $3.05^{xy}$ | $3.00^{xy}$ | $2.87^y$ | $2.95^{xy}$ | 0.27 | 0.08 |
| BW end of Week 3, lb | 258.6 | 271.3 | 275.5 | 269.8 | 273.1 | 5.6 | 0.22 |
| Week 4-6 | | | | | | | |
| ADG, lb/day | 1.80 | 1.94 | 1.93 | 2.14 | 1.87 | 0.15 | 0.69 |
| ADFI, lb/day | 7.65 | 8.11 | 7.79 | 7.41 | 7.50 | 0.48 | 0.77 |
| F:G | 4.37 | 4.18 | 4.07 | 3.49 | 4.02 | 0.26 | 0.38 |
| BW end of Week 6, lb | 296.4 | 312.0 | 315.9 | 314.7 | 312.4 | 7.9 | 0.41 |
| Week 1-6 | | | | | | | |
| ADG, lb/day | 1.90 | 2.27 | 2.36 | 2.33 | 2.28 | 0.19 | 0.41 |
| ADFI, lb/day | 7.47 | 7.89 | 7.90 | 7.29 | 7.63 | 0.38 | 0.80 |
| F:G | $3.85^x$ | $3.51^{xy}$ | $3.35^{xy}$ | $3.12^y$ | $3.34^{xy}$ | 0.22 | 0.16 |
| Carcass characteristics | | | | | | | |
| HCW, lb | 228.5 | 234.2 | 240.5 | 239.9 | 239.8 | 5.2 | 0.53 |
| Carcass yield, % | 76.9 | 75.3 | 76.2 | 76.3 | 76.7 | 0.8 | 0.73 |
| Loin eye area, in$^2$ | 9.3 | 9.9 | 7.6 | 9.9 | 9.4 | 1.0 | 0.56 |
| 10$^{th}$ Rib fat thickness, in | 1.00 | 0.70 | 0.73 | 0.54 | 0.59 | 0.13 | 0.50 |
| FA profile of backfat, % of total fat | | | | | | | |
| SFA | $37.1^a$ | $43.3^b$ | $40.9^{ab}$ | $40.9^{ab}$ | $40.4^{ab}$ | 1.3 | 0.003 |
| MUFA | $40.9^a$ | $35.2^{bc}$ | $34.3^{bc}$ | $34.8^{bc}$ | $36.6^{ab}$ | 1.3 | 0.0004 |
| PUFA | 20.4 | 20.0 | 22.6 | 22.4 | 20.8 | 1.0 | 0.14 |
| C18:0/C18:1 (indicator of Δ-9 desaturase activity) | $0.32^a$ | $0.53^b$ | $0.47^{ab}$ | $0.49^b$ | $0.46^{ab}$ | 0.04 | 0.0002 |
| Expected from CPFA | | 5.8 | | 3.23 | 3.37 | | |
| Expected from CLA | | | 4.02 | 1.85 | 2.91 | | |
| Expected IV | | 5.8 | 4.02 | 5.08 | 6.28 | | |
| IV$^2$ | $67.8^a$ | $62.0^b$ | $65.1^{ab}$ | $65.5^{ab}$ | $64.1^{ab}$ | 1.5 | 0.02 |

$^{a, b, c}$Means without a common superscript differ (P < 0.05)
$^{x, y}$Means without a common superscript tend to differ (P < 0.10)
$^2$Iodine value of backfat was calculated using the following equation (AOCS, 1998): IV = (C16:1 × 0.95) + (C18:1 × 0.86) + (C18:2 × 1.732) + (C18:3 × 2.616) + (C20:1 × 0.785) + (C22:1 × 0.723).

The invention illustratively disclosed herein suitably may be practiced in the absence of ay element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the disclosure are deemed to be covered by the disclosure, which is limited only by the claims which follow.

What is claimed is:

1. A method for improving growth aspects in a non-human animal, the method comprising the step of administering a feed composition for non-human animals comprising at least one conjugated linoleic acid (CLA) and at least one cyclo-propenoid fatty acid (CPFAs) to a non-human animal, wherein after administration to the non-human animal, the non-human animal shows improved growth aspects not exhibited by feed compositions comprising CLA alone,
   wherein the average daily intake of the at least one CLA ranges from about 1.0 g/day to about 10.0 g/day for the non-human animal, and
   wherein the average daily intake of the at least one CPFA ranges from about 0.1 g/day to about 1.0 g/day for the non-human animal.

2. The method of claim 1, wherein the improved growth aspects are measured by an increase in the average daily weight gain (ADG), improvement in feed conversion, reduced health issues, reduced mortality, or combinations thereof.

3. The method of claim 1, wherein the feed composition is administered to the non-human animal at least once per day.

4. The method of claim 1, wherein the non-human animal is selected from a group comprising pigs, cattle, poultry, alpaca, bison, camel, donkey, goat, horse, llama, mule, rabbit, sheep, goat, deer, aquaculture fish, aquaculture crustaceans, aquaculture mollusks, aquaculture echinoderms, or combinations thereof.

5. A method for increasing carcass gain and repartitioning nutrients to muscles (nitrogen retention) in a non-human animal, the method comprising the step of administering a feed composition for non-human animals comprising at least one conjugated linoleic acid (CLA) and at least one cyclopropenoid fatty acid (CPFAs) to the non-human animal, wherein after administration to the non-human animal, the non-human animal shows increased carcass gain and repartitioned nutrients to muscles (nitrogen retention) not exhibited by feed compositions using CLA alone,
wherein the average daily intake of the at least one CLA ranges from about 1.0 g/day to about 10.0 g/day for the non-human animal, and
wherein the average daily intake of the at least one CPFA ranges from about 0.1 g/day to about 1.0 g/day for the non-human animal.

6. The method of claim 5, wherein increased carcass gain and repartitioning nutrients to muscles (nitrogen retention) are measured by heavier hot carcass weight, greater carcass weight gain than total weight gain, increase loin depth, reduced back fat, increased carcass yield, increased lean percentage, or combinations thereof.

7. The method of claim 5, wherein the feed composition is administered to the non-human animal at least once per day.

8. The method of claim 5, wherein the feed composition is administered at least once per day.

9. The method of claim 5, wherein the non-human animal is selected from a group comprising pigs, cattle, poultry, alpaca, bison, camel, donkey, goat, horse, llama, mule, rabbit, sheep, goat, deer, aquaculture fish, aquaculture crustaceans, aquaculture mollusks, aquaculture echinoderms, or combinations thereof.

10. A method for controlling carcass iodine value (IV) in a non-human animal, the method comprising the step of administering a feed composition for non-human animals comprising at least one conjugated linoleic acid (CLA) and at least one cyclopropenoid fatty acid (CPFAs) to the non-human animal, wherein after administration to the non-human animal, the non-human animal shows a decrease in the carcass iodine value not exhibited by feed compositions using CLA alone,
wherein the average daily intake of the at least one CLA ranges from about 1.0 g/day to about 10.0 g/day for the non-human animal, and
wherein the average daily intake of the at least one CPFA ranges from about 0.1 g/day to about 1.0 g/day for the non-human animal.

11. The method of claim 10, where iodine value is decreased 1 point for each 40 grams to 70 grams of a composition containing 7.4% of the at least one CPFA and 92.6% of the at least one CLA.

12. The method of claim 10, wherein the controlled iodine value is measured by a decrease in the carcass iodine value, increasing saturated fatty acids, reducing mono- and polyunsaturated acid in the fat, decreasing delta-9 desaturase activity, reduction in carcass unsaturated fat content, increased melting point of the carcass, improved carcass hardness, jowl firmness, backfat firmness, stick to belly fat, or combinations thereof.

13. The method of claim 10, wherein the feed composition is administered at least once per day tor the non-human animal.

14. The method of claim 10, wherein the non-human animal is selected from a group comprising pigs, cattle, poultry, alpaca, bison, camel, donkey, goat, horse, llama, mule, rabbit, sheep, goat, deer, aquaculture fish, aquaculture crustaceans, aquaculture mollusks, aquaculture echinoderms, or combinations thereof.

* * * * *